(12) United States Patent
Qian

(10) Patent No.: US 9,761,340 B2
(45) Date of Patent: Sep. 12, 2017

(54) METHOD OF PREPARING STRAIN RELEASED STRIP-BENT X-RAY CRYSTAL ANALYZERS

(71) Applicant: Qing Qian, Freehold, NJ (US)

(72) Inventor: Qing Qian, Freehold, NJ (US)

( * ) Notice: Subject to any disclaimer, the term of this patent is extended or adjusted under 35 U.S.C. 154(b) by 0 days.

(21) Appl. No.: 15/275,430

(22) Filed: Sep. 25, 2016

(65) Prior Publication Data

US 2017/0110621 A1    Apr. 20, 2017

Related U.S. Application Data

(60) Provisional application No. 62/243,117, filed on Oct. 18, 2015.

(51) Int. Cl.
*H01L 31/08* (2006.01)
*H01L 31/18* (2006.01)
*G01N 23/207* (2006.01)
*G21K 1/00* (2006.01)

(52) U.S. Cl.
CPC ............ *G21K 1/00* (2013.01); *G01N 23/2076* (2013.01); *H01L 31/085* (2013.01); *H01L 31/1804* (2013.01)

(58) Field of Classification Search
CPC .... G21K 1/00; G01N 23/2076; H01L 31/085; H01L 31/1804
USPC .......................................................... 438/64
See application file for complete search history.

*Primary Examiner* — Caleen Sullivan

(57) ABSTRACT

A method of preparing two dimension bent X-ray crystal analyzers in strips feature is provided. A crystal wafer in strips is bonded to a curved substrate which offers the desired focus length. A crystal wafer in strips is pressed against the surface of the substrate forming curved shape by anodic bonding or glue bonding. The bonding is permanently formed between crystal wafer and its substrate surface, which makes crystal wafer has same curvature as previously prepared substrate.

9 Claims, 5 Drawing Sheets

Figure 1
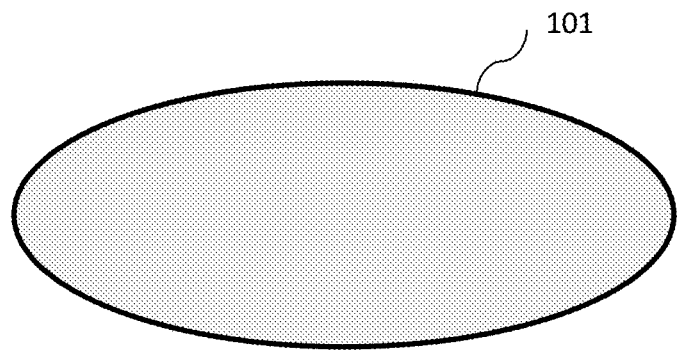
FIG.1A
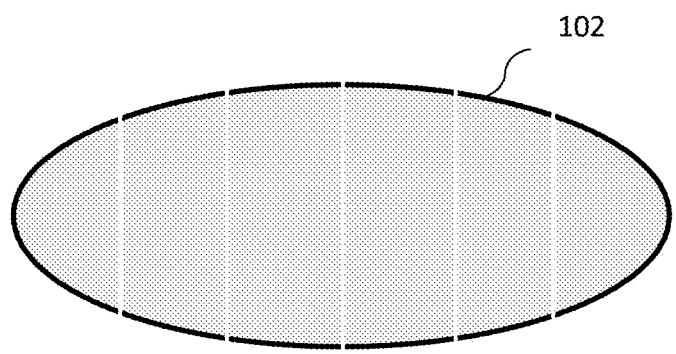
FIG1.B
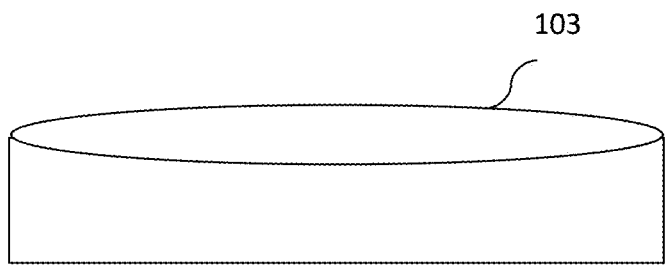
FIG.1C

METHOD OF PREPARING STRAIN RELEASED STRIP-BENT X-RAY CRYSTAL ANALYZERS

CROSS-REFERENCE TO RELATED APPLICATIONS

This application claims priority to and the benefit of U.S. provisional patent application Ser. No. 62/243,117, filed Oct. 18, 2015, which application is incorporated herein by reference in its entirety.

TECHNICAL FIELD

The present invitation is directed generally to x-ray bent crystal analyzers, in particular, but not necessarily exclusively to spherically bent crystal analyzers.

BACKGROUND OF THE INVENTION

X-ray crystal analyzer is widely used in x-ray wavelength dispersed detection system, such as in wavelength dispersed x-ray fluorescence system (WDXRF), x-ray emission spectroscopy system (XES), fluorescence model x-ray absorption spectroscopy system (XAS) and extended x-ray fine structure system (EXFS). All these kind of crystal analyzers are based on Bragg's diffraction law. They are normally made from single crystals, or multiple layers. In order to increase detecting efficiency, they are machined and bent in one dimension or two dimensions with some shapes. And analyzers curved in two dimensions are much better than in one dimension both in energy resolution, efficiency and lower background, but more difficulty. Such crystal analyzers can be employed in the Rowland circle with either the Johann or Johansson geometries, for wavelength-specific focusing of x-rays in diffraction way. For applications, a radius of curvature of one meter is typically required.

Normally, a quite lot of crystal analyzers are made in bending crystal wafers to curved substrates by glue or anodic bonding method. Due to strong strain force from crystal wafers in bending, it is always quite difficult to get good energy resolution in two dimension bent analyzers. Although there exist dicing-bent spherical crystal analyzers, the efficiency is always reduced due to a partial crystal area diced off. So, two dimension bent crystal analyzer in full size with less strain is a big advantage to x-ray spectrometers.

BRIEF SUMMARY OF THE INVENTION

In manufacturing two dimension bent x-ray crystal analyzers, we invented a new method—strip wafer bonding method. Differ from classical ways, in which people always keep a crystal wafer in complete one when bonding to a substrate. But we cut the crystal wafer in strips, and bond them to the substrate while keeping them in same position as their own before cut. That new method can reduce crystal strain in bending, that leads to better energy resolution, and keeps full size area without losing detection efficiency.

BRIEF DESCRIPTION OF DRAWINGS

The foregoing and other objects, aspects and advantages will be better understood from the following detailed description of a preferred embodiment of the invention with reference to the drawings, in which:

FIG. 1 is a schematic drawing of materials preparing as following in manufacturing Crystal analyzer: FIG. 1A. crystal wafer 101 for bonding; FIG. 1B. wafer is cut to several strips 102, here 6 strips; FIG. 1C. concave substrate 103;

DETAILED DESCRIPTION

The present disclosure relates a method which can help to prepare any focus length crystal analyzers bent in two dimensions, which based on silicon or germanium crystal wafers, but not only limit to them. This invention works on crystal wafers which can be bonded by anodic bonding or glue bonding method, such as silicon and germanium crystals. Anodic bonding will get better quality.

Here we describe this invention in anodic bonding method in details:

Preparing double or single side polished crystal wafers for anodic bonding in thin thickness, which is based on focus length needed. Thickness of the wafer can be chose as $T/F<10^{-3}$. Where T is crystal wafer thickness and F is focus length in need. See 101 in FIG. 1A.

Cut crystal wafer 101 in strips but keep all strips in same order as in a whole wafer. See 102 in FIG. 1B.

Preparing optical grade polished glass substrate 103 in FIG. 1C, which is suitable for anodic bonding and have similar thermal expansion coefficient as bonding crystal wafers. Machining these substrate's one side surface to concave curved shape as needed and leave the other side flat. The substrate's thickness is less than 20 mm on edge.

Figure 2:
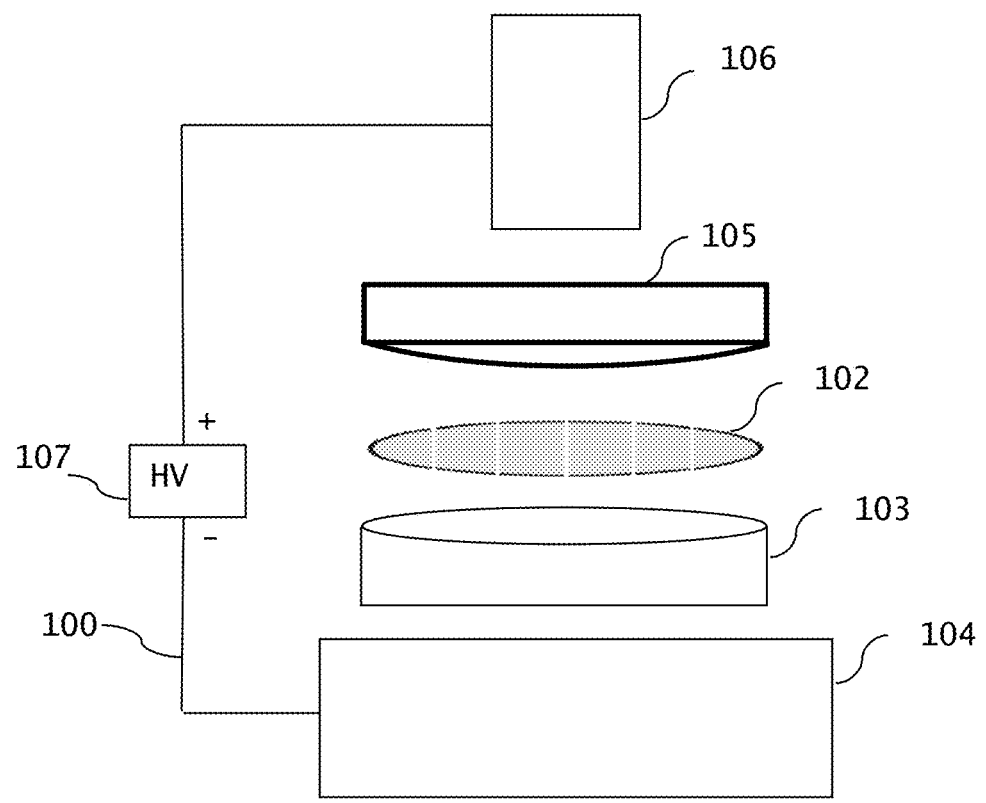
FIG. 2 is a schematic drawing of anodic bonding system for crystal analyzers. 102—wafers strips; 103—concave glass substrate; 104—hotplate; 105—curved die for pressing, forcing the flat crystal wafer strips to match the substrate curved surface; 106—pressor with pressure on; 107—high voltage power supplier; 100—electric wires.

Set the substrate on a hotplate 104 at temperature between 250° C. and 400° C. with crystal wafer strips on its top. See FIG. 2.

Applying force on pressor 106 then to a convex die 105 on top of this setting, where 105 has same curved shape as the substrate 103. Increasing force until tightly contacting wafer 102 and substrate 103 together.

Applying high voltage 107 on the crystal wafer and its substrate. The voltage can be as high as 1000V to 3000V, and current 1 mA to 40 mA dependent on substrate thickness and the force applied.

Normally it takes 3-10 minutes for bonding. Waiting for another 90 minutes or longer for solid after it was bonded.

Figure 3:
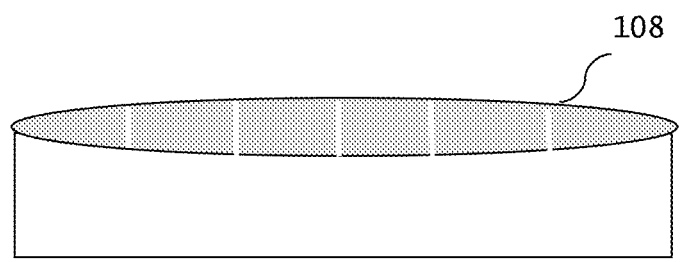
FIG. 3 crystal wafer strips are bonded to concave substrate 105.

Cooling down the bonded crystal analyzer 108 on site to room temperature in air. See FIG. 3.

Figure 4:
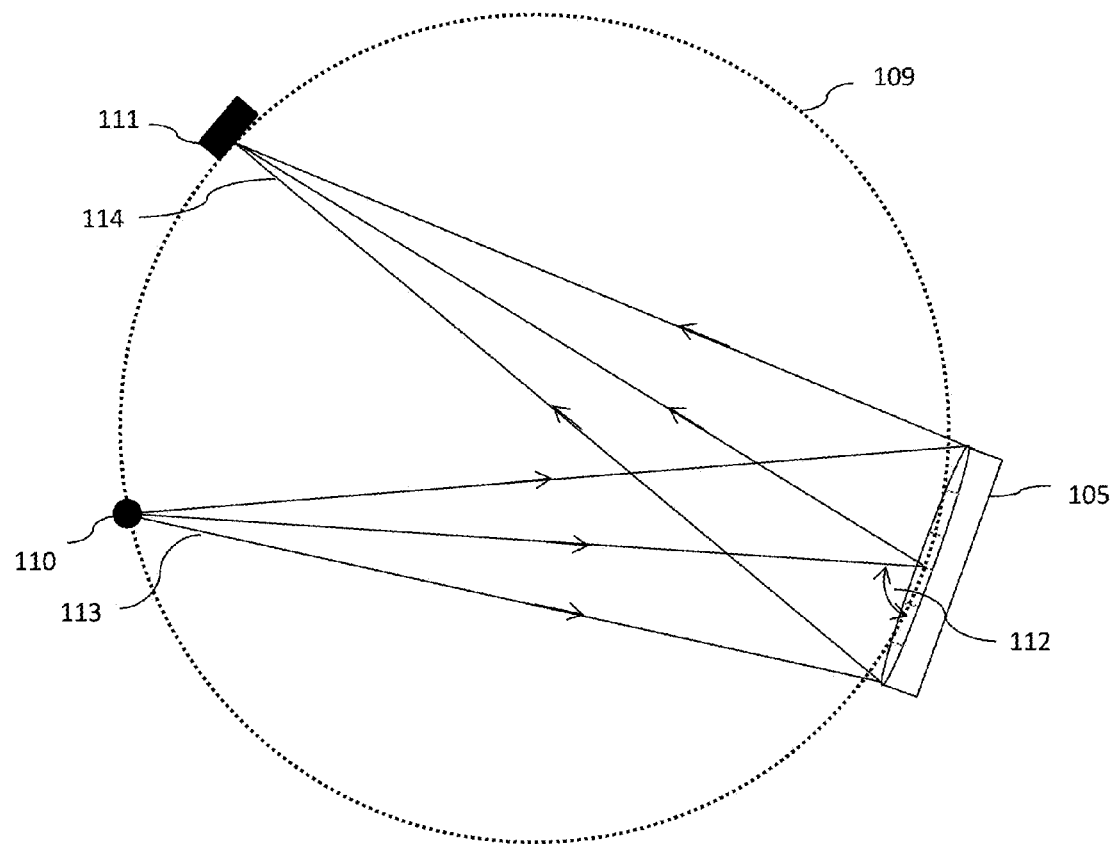
FIG. 4 is a schematic drawing of Johann type strip-bent crystal analyzer used in x-ray spectrometer of Rowland circle geometry. 109—Rowland circle; 110—sample measured in x-ray; 111—x-ray detector; 105—strip-bent crystal analyzer; 112—Bragg's angle; 113—emitted or scattered x-rays; 114—diffracted x-rays.
Figure 5:
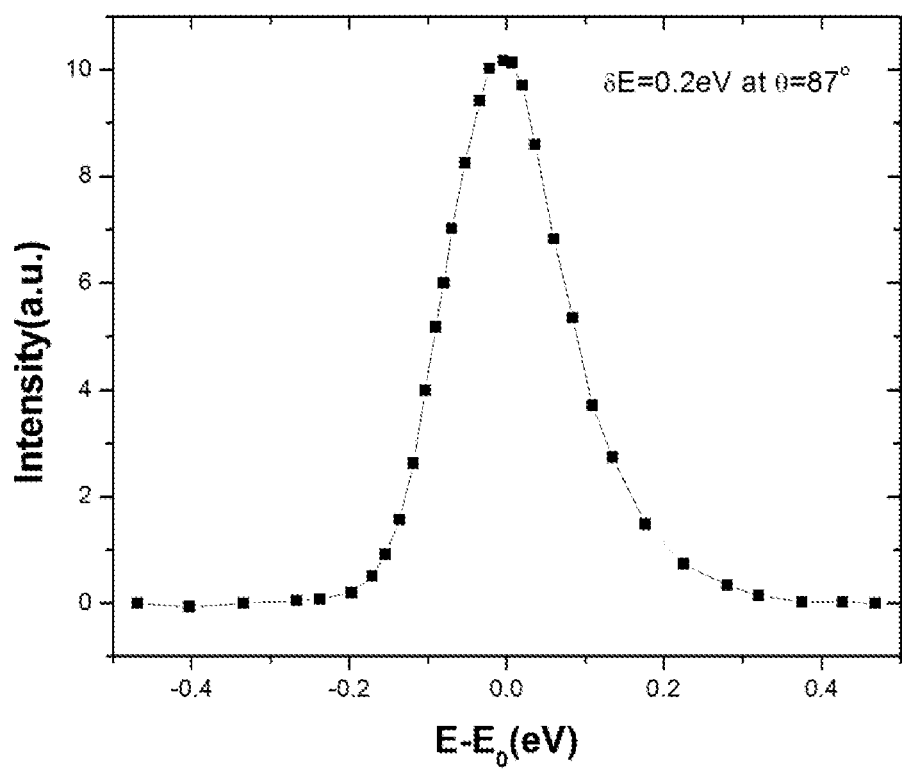
FIG. 5 is a plot of x-ray elastic scanning with a silicon crystal strip-bent analyzer to check analyzer properties. It is measured with incident energy at 7919 eV, Bragg's angle at 87°, it gives energy resolution around 0.2 eV.

The crystal analyzer 108 is normally employed in the Rowland circle with either the Johann or Johansson geometries, for wavelength-specific focusing of X-rays in diffraction way. Here FIG. 4 shows a schematic drawing of Johann type Strip-bent crystal analyzer used in x-ray spectrometer of Rowland circle geometry. X-rays emitted or scattered from target sample 110 are collected by strip-bent crystal analyzer 105. After diffracting in 105, those diffracted x-rays get into a x-ray detector 111. Both count rates and Bragg's angles are recorded and plotted out to form x-ray spectra. One plot in FIG. 5 is x-ray elastic scanning of silicon crystal strip-bent analyzer Si(444). It is measured with incident energy at 7919 eV, Bragg's angle at 87°, it gives energy resolution around 0.2 eV.

The invention claimed is:

1. A Method of making x-ray crystal analyzer in two dimension bending with strip crystal feature by bonding crystal wafer in strips with curved substrate.

2. The method of claim 1, wherein the bonding method is anodic boing, it comprising: pressing the top crystal wafer strips and substrate together, heating all set to high temperature, applying high voltage on wafer and its substrate, forming chemical atomic bond between the crystal wafer and its glass substrate.

3. The method of claim 2, wherein the crystal wafer strips can be bonded one by one, or bonded all in same time.

4. The method of clam 1, wherein the bonding method can be glue method or others, in which, it can bond crystal wafer and substrate together.

5. The method of claim 4, wherein there can be a interlayer between wafer strips and substrate.

6. The method of claim 1, wherein the crystals can be silicon, germanium, sapphire, quartz, lithium fluoride, diamond, Lithium Niobium oxide and all crystals which can be sliced and bent.

7. The method of claim 1, wherein the substrate can be metal and glass.

8. The method of claim 1, wherein the crystal wafer can be cut in any shape and any pieces, but are aligner in their original position in the wafer.

9. The method of claim 1, wherein the bending radius can be any length between 10 mm to 3000 mm.

* * * * *